United States Patent
Holthuizen et al.

(10) Patent No.: US 11,497,562 B2
(45) Date of Patent: Nov. 15, 2022

(54) POSITION DETECTION BASED ON TISSUE DISCRIMINATION

(71) Applicant: KONINKLIJKE PHILIPS N.V., Eindhoven (NL)

(72) Inventors: Ronaldus Frederik Johannes Holthuizen, Odijk (NL); Bernardus Hendrikus Wilhelmus Hendriks, Eindhoven (NL); Drazenko Babic, Best (NL); Robert Johannes Frederik Homan, Batenburg (NL); Johan Juliana Dries, Arendonk (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 94 days.

(21) Appl. No.: 16/483,951

(22) PCT Filed: Feb. 7, 2018

(86) PCT No.: PCT/EP2018/052989
§ 371 (c)(1),
(2) Date: Aug. 6, 2019

(87) PCT Pub. No.: WO2018/146112
PCT Pub. Date: Aug. 16, 2018

(65) Prior Publication Data
US 2020/0085506 A1    Mar. 19, 2020

(30) Foreign Application Priority Data
Feb. 9, 2017   (EP) .................................... 17155320

(51) Int. Cl.
*A61B 34/20* (2016.01)
*A61B 34/10* (2016.01)
(Continued)

(52) U.S. Cl.
CPC ............ *A61B 34/20* (2016.02); *A61B 5/0035* (2013.01); *A61B 5/0084* (2013.01);
(Continued)

(58) Field of Classification Search
CPC ......... A61B 34/20; A61B 34/10; A61B 90/37; A61B 5/0035; A61B 5/0084;
(Continued)

(56) References Cited

U.S. PATENT DOCUMENTS 6,470,207 B1 * 10/2002 Simon .................... G16H 40/63
600/426
2009/0163901 A1   6/2009 Fisher et al.
(Continued)

OTHER PUBLICATIONS

Mobbs et al. "Technique, Challenges and Indications for Percutaneous Pedicle Screw Fixation" Journal of Clinical Neuroscience 18 (2011) p. 741-749.
(Continued)

*Primary Examiner* — Rene T Towa

(57) ABSTRACT

A system is suggested comprising an optical sensing means and a processing unit. The optical sensing means may include an optical guide with a distal end, wherein the optical guide may be configured to be arranged in a device to be inserted into tissue in a region of interest. The processing unit may be configured to receive information of a region of interest including different tissue types as well as of a path through the tissues, to determine a sequence of tissue types along the path, to determine a tissue type at the distal end of the optical guide based on information received from the optical sensing means, to compare the determined tissue type with the tissue types on the path, to determine possible positions of the distal end of the optical guide on the path based on the comparison of tissue types, and to generate a signal indicative for the possible positions.

11 Claims, 5 Drawing Sheets

(51) Int. Cl.
*A61B 5/00* (2006.01)
*A61B 17/70* (2006.01)
*A61B 17/88* (2006.01)
*A61B 90/00* (2016.01)

(52) U.S. Cl.
CPC ...... *A61B 17/7032* (2013.01); *A61B 17/8897* (2013.01); *A61B 34/10* (2016.02); *A61B 90/37* (2016.02); *A61B 2034/102* (2016.02); *A61B 2034/2051* (2016.02); *A61B 2034/2055* (2016.02); *A61B 2034/2061* (2016.02); *A61B 2034/2065* (2016.02); *A61B 2090/374* (2016.02); *A61B 2090/376* (2016.02); *A61B 2090/378* (2016.02); *A61B 2090/3762* (2016.02)

(58) Field of Classification Search
CPC ............ A61B 17/7032; A61B 17/8897; A61B 2034/102; A61B 2034/2051; A61B 2034/2055; A61B 2034/2061; A61B 2034/2065; A61B 2090/374; A61B 2090/376; A61B 2090/3762; A61B 2090/378; A61B 2090/371; A61B 2090/3735; A61B 5/0033; A61B 5/065; A61B 2017/00061; A61B 2090/364; A61B 2090/062; A61B 2034/107; A61B 2090/373; A61B 17/70; A61B 17/864; A61B 5/0075

See application file for complete search history.

(56) References Cited

U.S. PATENT DOCUMENTS

| | | | |
|---|---|---|---|
| 2009/0221922 A1* | 9/2009 | Lee | A61B 5/0084 600/478 |
| 2011/0196376 A1 | 8/2011 | Ozgur | |
| 2012/0059251 A1* | 3/2012 | Bakker | A61B 17/34 600/424 |
| 2012/0109133 A1 | 5/2012 | Neubardt et al. | |
| 2012/0232407 A1 | 9/2012 | Fisher et al. | |
| 2014/0187917 A1 | 7/2014 | Clark | |
| 2014/0316280 A1* | 10/2014 | Mueller | A61B 18/1492 600/476 |
| 2015/0080711 A1* | 3/2015 | Hendriks | A61B 5/0075 600/424 |
| 2015/0080712 A1 | 3/2015 | Van Keersop et al. | |
| 2015/0110374 A1* | 4/2015 | Traughber | G01R 33/481 382/131 |
| 2016/0166337 A1 | 6/2016 | Markey et al. | |
| 2017/0348056 A1* | 12/2017 | Steinle | G06T 7/0012 |

OTHER PUBLICATIONS

International Search Report From PCT/EP2018/052989 dated Feb. 7, 2018.

* cited by examiner

POSITION DETECTION BASED ON TISSUE DISCRIMINATION

CROSS-REFERENCE TO PRIOR APPLICATIONS

This application is the U.S. National Phase application under 35 U.S.C. § 371 of International Application No. PCT/EP2018/052989, filed on Feb. 7, 2018, which claims the benefit of European Patent Application No. 17155320.9 filed on Feb. 9, 2017. These applications are hereby incorporated by reference herein.

FIELD OF THE INVENTION

The invention generally relates to a system and a method for detection of biological tissue types. The invention further relates to a system and a method for detection of a position of a device in tissue based on a determination of different tissue types. The invention further relates to a computer program causing a system to perform steps of a method resulting in a detection of a position of a device within tissue based on a determination of tissue types.

BACKGROUND OF THE INVENTION

For example, pedicle screw fixations are a mainstay in treatment of spinal degenerative disease, intervertebral disc disease, spinal traumas or spinal deformities. Pedicle screw fixation provides short, rigid segmental stabilization that allows preservation of motion segments and stabilization of the spine. Fusion rates and clinical outcome in the treatment of thoracolumbar fractures appear to be superior to that achieved using other forms of treatment. According to a report by the Agency for Healthcare Research and Quality (AHRQ), approximately 488,000 spinal fusions were performed during U.S. hospital stays in 2011 (a rate of 15.7 stays per 10,000 population), which accounted for 3.1% of all operating room procedures.

The safety and the effectiveness of pedicle-screw instrumentation in the spine have been questioned despite its use worldwide to enhance stabilization of the spine. A major concern related to the pedicle screw placement is the accurate positioning of the pedicle screws. In fact, pedicle screws are inserted either more or less blindly or under often-poor fluoroscopic guidance resulting in rather poor clinical outcomes so far.

It will be understood that comparable problems may occur also in other fields of bone treatment. US 2012/232 407 describes methods and devices for navigating through bone. In one embodiment, a bone navigation device is provided and includes a bone penetrating member configured to be implanted in bone and having at least one optical waveguide extending therethrough. The optical waveguide is adapted to illuminate tissue surrounding the device and to receive reflected/transmitted light from the tissue to determine the optical characteristics of the tissue.

SUMMARY OF THE INVENTION

It may be seen as an object to determine a position of a device being inserted into a region of interest based on tissue types. This and other objects are solved by the system and the computer program according to the independent claims, respectively. Further embodiments are described in the dependent claims.

In other words, it may be seen as an object to provide a device placement system that can detect in an early stage whether the device is misplaced such that redirection of the device is still possible.

To solve the above-mentioned problems, a device placement system according to an embodiment may be provided comprising an imaging system and a planning and navigation system. The imaging system may be capable of generating an image of a region of interest, for example of a spine, and the planning and navigation system may be adapted for a planning of an insertion of a device into the region of interest, for example of an insertion of a pedicle screw in one of the vertebra of the spine. On the one hand, the tissue types that may be encountered during a device placement are stored in a table. On the other hand, a navigation system, which at least provides information assisting in guiding the device placement, may determine an actual position of the device based on a determination of the tissue at or in front of the device and based on the sequence of tissue types stored in the table. This may be done based on a real-time tissue sensing which may be performed by the device being inserted into the region of interest. Such a device may be a k-wire, an awl or a tap, or a screw. The system may thus compare a predicted tissue type determined by means of imaging and during planning with a real-time measured tissue type determined by means of sensing.

A system according to an embodiment may comprise an optical sensing means and a processing unit. The optical sensing means may include an optical guide with a distal end, wherein the optical guide may be configured to be arranged in a device to be inserted into tissue in a region of interest. The distal end of the optical guide may be arranged adjacent to a leading end of the device. The processing unit may be configured (i) to receive information of a region of interest including different tissue types, (ii) to receive an input identifying a path through the region of interest, (iii) to determine a sequence of tissue types along the path, (iv) to receive optical information from the optical sensing means, (v) to determine a tissue type at the distal end of the optical guide based on the received optical information, (vi) to compare the determined tissue type with the tissue types on the path, (vii) to determine possible positions of the distal end of the optical guide on the path based on the comparison of tissue types, and (viii) to generate a signal indicative for the possible positions.

The generated signal may be used by the user, for example a physician, to determine whether the device placement is still correct. An increased difference would mean that the tip of the device is not at the predicted position. In case of an insertion of a pedicle screw, this may be caused by local tissue deformation or by displacement of a vertebra with respect to the outside surface of the patient.

According to an embodiment, the system may further comprise a tracking device for tracking a position of the distal end of an optical guide relative to the region of interest, wherein determination of the possible positions is further based on the tracked position. It will be understood that the distal end may be tracked by identifying a spatial position and orientation of a proximal end of a device and based on a known geometry of the device, i.e. based on a known distance between the identified proximal end and the distal end. For an identification of a proximal end, the tracking device may comprise at least one tracking camera and for example a shaft marker and/or a tracer plate at the device, wherein a position and orientation of the shaft marker and/or the tracer plate is identifiable on the basis of images generated by the at least one camera. Apart from camera based tracking systems, solutions like optical shape sensing and EM (electromagnetic) tracking can be applied. Furthermore, the body of the patient may also be tracked to determine any changes of the patient' position on a table. A combination of both trackings may improve the results. Detailed information regarding tracking devices can be taken for example from pages 23 to 44 of T. Peters and K. Cleary, "Image-Guided Interventions" (2008, Springer-Science+Business Media, LLC).

Thus, even if markers of a tracking system are present and a difference between the predicted and the sensed position is due to an inaccuracy of the tracking system, an indication of an early detection of misplacement of a device may be provided, in particular before critical structures are reached.

According to a further embodiment, the system may generate a signal indicative for a mismatch between a determined tissue type based on optical information received from an optical sensing means, and the possible tissue types along a path through the region of interest. The signal may be an optical signal like a flash light or just a text on a screen or may be an acoustic signal like an alarm.

According to an embodiment, the processing unit of the system may further be configured to generate a visualization of the region of interest together with a virtual representation of an element to be inserted, in the region of interest, wherein the distal end of the virtual representation of the element is shown at the most probable position on the path. Such visualization may also be suitable for planning an insertion, as the virtual representation allows defining a path for an insertion and thus a sequence of tissues along that path.

According to another embodiment, the system may further comprise a video camera for imaging an operation field including the region of interest, wherein the processing unit is further configured to generate a combined visualization of the operation field and of inner structures of the region of interest. For example, the outer structure imaged by the video camera may be visualized with a degree of transparency allowing recognition of outer structures and at the same time of inner structures lying beneath these outer structures, i.e. inside the body.

According to an embodiment, the system may further comprise an imaging system for generating information of a region of interest including different tissue types, wherein the imaging system is one out of the group consisting of an X-ray imaging system, an MR imaging system, a CT imaging system, and an ultrasound imaging system. The system may further comprise an input device, wherein for example an intended path for an insertion may be entered. Additionally and/or alternatively, the system may suggest a path automatically based on predefined criteria including for example requirements of enough stable tissue for a sufficient fixation of the device to be inserted, as well as of anatomical structures which must be avoided like nerves.

According to an embodiment, the system comprises a video camera and an X-ray imaging system, for example a C-arm based X-ray system, wherein the video camera may be attached to the detector of an X-ray system.

According to an embodiment, the system may further comprise an instrument for inserting the device into the region of interest, for example a bone, wherein a position and orientation of the instrument is traceable by a tracking device. A visualization may be generated including an indication of a relation of the instrument to the region of interest, without exposing the patient with x-ray radiation.

The systems according to the mentioned embodiments is adapted to detect mismatches between the predicted tissue properties based on imaging and navigation and measured tissue properties based on tissue sensing. In such cases intra-operative imaging must only be used to update the planning and/or registration of the navigation system to ensure correct placement of for example a screw in an early stage. Consequently, the X-ray radiation may be reduced and the placement of a device in a tissue may be improved at the same time.

According to a further embodiment, a pedicle screw placement system comprises an imaging system capable of making an image of the interior of the body, a planning software capable of defining an insertion path based on the interior image, an algorithm generating a table of tissue properties that will be encountered during the planned insertion, a navigation system that assists in placing the screw according to the planned insertion, a real-time tissue sensor incorporated in the device to be inserted, for example a screw, k-wire, awl and/or tap, capable of determining real-time the tissue properties in front of the device, a processing unit capable of comparing the predicted tissue type based on the planned insertion path and the measured tissue type according to the real-time tissue sensor, wherein a signal may be generated indicative for the difference between the real-time measured tissue and the tissue type according to the predicted tissue type based on the planned device (screw) insertion.

According to an embodiment, a system for detection of optical properties of tissue may comprise a light source, a light detector, a probe and a processing unit. The probe may have a shaft with a longitudinal axis and a front end, and at least one fibers, wherein an end of the fiber is arranged at the front end of the shaft. The fiber may be adapted to transmit light emitted from the light source to a tissue adjacent to the front end of the shaft and may be adapted to transmit light reflected from the tissue to the light detector. With more than one fiber a light path through the tissue may be defined. The processing unit may be configured (i) to control the light source to emit light, (ii) to receive a signal generated by the light detector based on the light reflected by the tissue, (iii) to determine a light spectrum of the reflected light, based on the received signal, and (iv) to compare at least two spectra. For example, the reflected light may be transferred to a spectrometer.

It should be noted that the end surface of an optical fiber at an opening in the front surface may have a circular shape or a more or less oval shape in case of a substantially circular cross section of the fiber in an inclined front surface. Depending on the angle at which the fiber ends at the bevel surface, the shape of the end surface of the fiber will be effected and therefore also the direction of the emitted or received light.

A pair of fiber ends may define a light path, with light emitted from a first fiber, reflected in tissue and received in a second fiber of the pair. Depending on the position of the respective fiber ends, the light path will have a spatial orientation relative to the shaft of the probe. The spatial orientation will differ as soon as different fibers form a pair or as soon as the probe is rotated.

According to an embodiment, the system may further comprise a console including the light source, the light detector and the processing unit for processing the signals provided by the light detector, the console being adapted for in-vivo tissue inspection and discrimination. The light source may be one of a laser, a light-emitting diode or a filtered light source, and the console may further comprise one of a fiber switch, a beam splitter or a dichroic beam combiner. Furthermore, the device may be adapted to perform at least one out of the group consisting of diffuse reflectance spectroscopy, diffuse optical tomography, differential path length spectroscopy, and Raman spectroscopy. The console may comprise at least one spectrometer.

According to another aspect, a method of determining a position of a device in tissue is proposed, comprising the steps of (i) determining a sequence of tissue types along a path identified in a region of interest, (ii) determining a tissue type at a distal end of an optical guide, (iii) comparing the determined tissue type with the tissue types on the path, and (iv) determining and indicating possible positions of the distal end of the optical guide on the path.

According to an embodiment, the method may further comprise the step of tracing the distal end of the optical guide by means of a tracking device. In such an embodiment, a determination of a possible position of the inserted device may also be based on the tracked position.

According to another embodiment, the method may further comprise the step of generating a visualization of the region of interest together with a virtual representation of an element to be inserted, in the region of interest, wherein the distal end of the virtual representation of the element is shown at the most probable position on the path.

The method may be an information processing method, wherein different information is combined with the aim to provide new information which new information may help a physician to treat a patient. Consequently, the method according to an embodiment does not include a step of treatment of a human or animal body by surgery. According to another aspect, the method may be implemented in form of sets of instruction of a computer program element which when executed on a processing unit of an above described system causes the system to perform the above mentioned method. Such a computer program element may preferably be loaded into a work memory of a data processor. The data processor is thus equipped to carry out the method. Further, the invention relates to a computer readable medium, such as a CD-ROM, at which the computer program may be stored. However, the computer program may also be presented over a network like the World Wide Web and can be downloaded into the work memory of a data processor from such a network.

The aspects defined above and further aspects, features and advantages of the present invention may also be derived from the examples of embodiments to be described hereinafter and are explained with reference to examples of embodiments. The invention will be described in more detail hereinafter with reference to examples of embodiments but to which the invention is not limited.

BRIEF DESCRIPTION OF THE DRAWINGS

The illustration in the drawings is schematically only and not to scale. It is noted that similar elements are provided with the same reference signs in different figures, if appropriate.

DETAILED DESCRIPTION OF EMBODIMENTS

Figure 1:
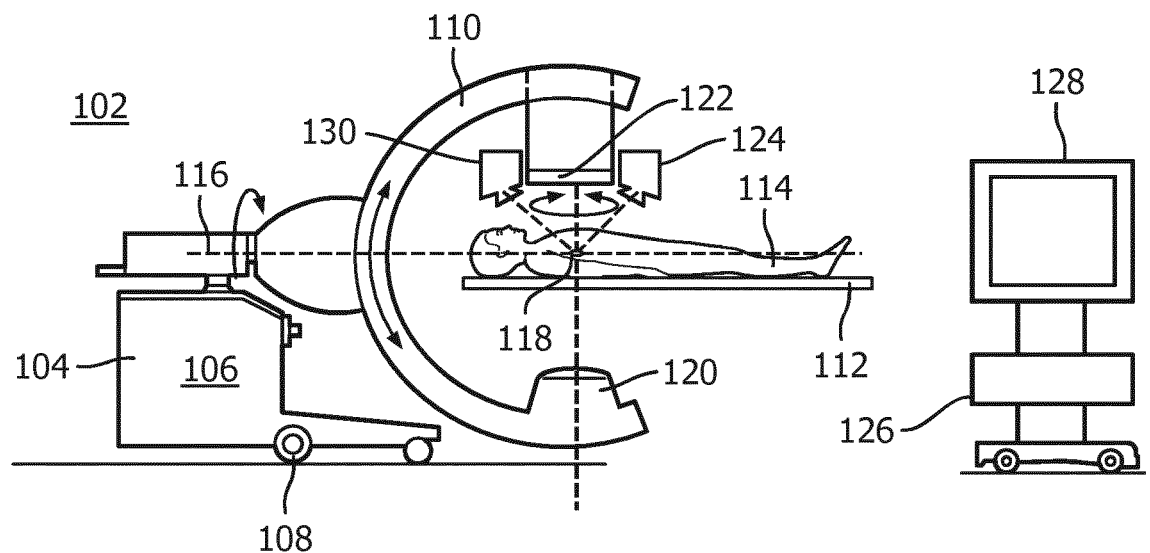
FIG. 1 shows a system according to an embodiment.

FIG. 1 is a schematically illustration of a system 102 comprising an X ray device 104 for providing X ray images of a patient's interior. The X ray device 104 has a base frame 106 supported by wheels 108, a movable C arm 110 and a patient's table 112 for supporting a patient 114. In this particular example, the patient 114 is a human being, but may also be an animal. The C arm 110 is rotatable with regard to a first axis 116, which axis has a direction corresponding to a main orientation of the surgical table 112, and to a second axis 118, which second axis is perpendicular to the first axis and parallel to the patient's table 112. An X ray source 120 and an X ray detector 122, which is preferably a rectangular and flat detector, are mounted on the C arm 110 such that the X ray source and the X ray detector reside opposite one another along the axis 118. A camera 124 for providing a stream of video images of a patient's exterior is mounted on the C arm 110 aside the X ray detector 122, wherein the camera 124 may be responsive for example to a first range of wavelengths in the visible spectrum. A further camera 130 for providing a further stream of camera images of the patient's exterior, may be additionally mounted on the C arm 110 aside the X ray detector 122, wherein the further camera 130 may be responsive to other wavelengths, for example to another range of wavelengths in the visible spectrum. Additionally and/or alternatively, the cameras 124 and 130 may be utilized for tracking a tracer plate at a device being in the field of view of the cameras.

The system further comprises a processing unit 126 and a monitor 128 for visualizing information, wherein the processing unit may be connected, on the one hand, with the X-ray device so that the processing unit may control a generation of X-ray images, and on the other hand, with the cameras 124 and 130 for controlling and receiving images from the cameras and/or for tracking a device. The processing unit may further be connected to a data base, wherein the processing unit may receive from the data base previously generated X-ray data as well as spectral information of specific tissues for comparison with spectra sensed during an insertion of a device into tissue.

Figure 2:
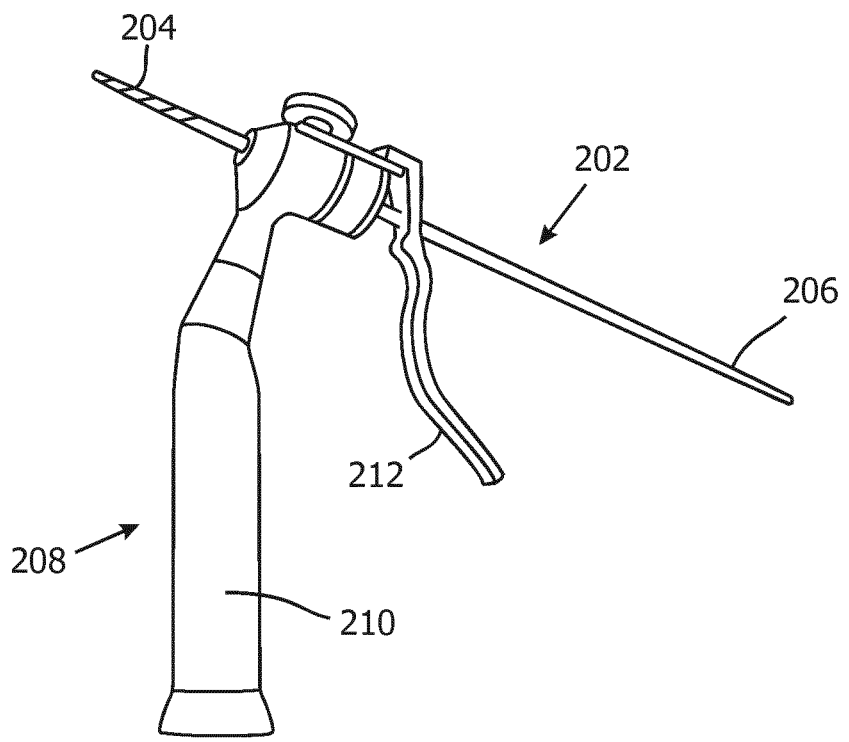
FIG. 2 shows a K-wire together with an inserting device.

FIG. 2 shows an embodiment of a device which may be inserted into tissue in a region of interest. In this embodiment, the device is a K-wire 202 with a leading end portion 204 and a trailing end portion 206, wherein the leading end portion 204 may be provided with a sharp tip and/or a thread facilitating an inserting of the K-wire into hard tissue like bone. The K-wire 202 may be inserted by an instrument 208 having a grip portion 210 and a handle 212, wherein a movement of the handle 212 towards the grip portion may push the K-wire forwards, i.e. in a direction of the leading end portion.

Figure 3:
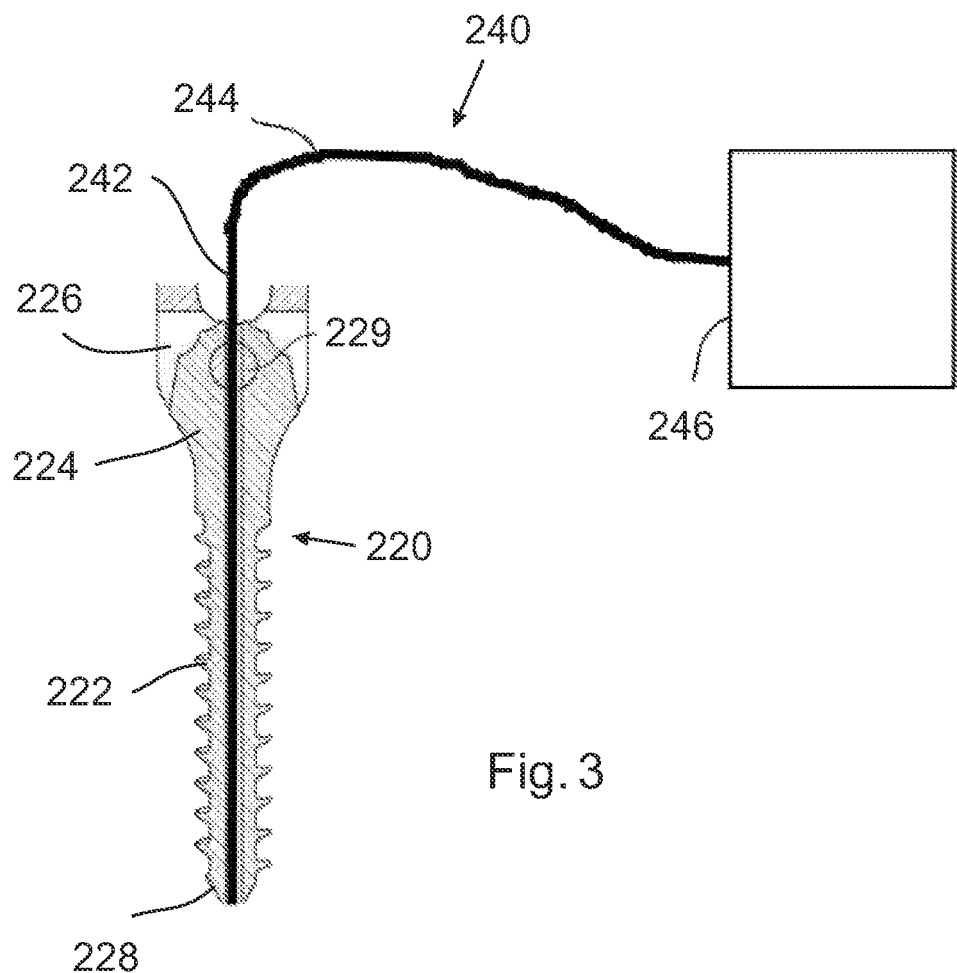
FIG. 3 shows a bone screw together with an optical sensing device.

FIG. 3 shows a pedicle screw 220 together with an optical sensing device 240. The pedicle screw 220 includes a body 222, a neck 224 and a head 226. The body 222 is provided with a thread having a pitch and an outer diameter and an inner diameter, such that the thread depth is the difference between the outer diameter and the inner diameter. The pedicle screw 220 has a hollow shaft, into which an optical probe or stylet 242 of the optical sensing device 240 may be inserted such that the optical probe or stylet 242 extends to the distal tip 228 of the screw 220. The stylet 242 and the whole optical sensing device 240 contain a waveguide such as an optical fiber 244 that is connected to an optical console 246 that is capable of sending and receiving light. The received light is spectrally analyzed allowing tissue discrimination at the tip of the screw 220. For instance techniques like diffuse reflectance spectroscopy, fluorescence spectroscopy, RAMAN spectroscopy, OCT can be applied. Specifically, the received light is used for a determination of the parameter indicative for, for example, the fat content of tissue in front of the tip of the screw 220 and the optical stylet 242, which, in turn, is used for determining whether the tissue, in case of a bone, is that of the soft(er) part of the bone or that of the hard(er) part of the bone, thereby allowing for a navigation assistance in placing the screw 220 in a bone. It will be understood that the optical console 246 may be connected with the processing unit 126 of the system shown in FIG. 1, so that also the information provided by the optical console may be processed by the processing unit and may be combined with the information received from other parts of the system like the X-ray device or a tracking device.

Figure 4:
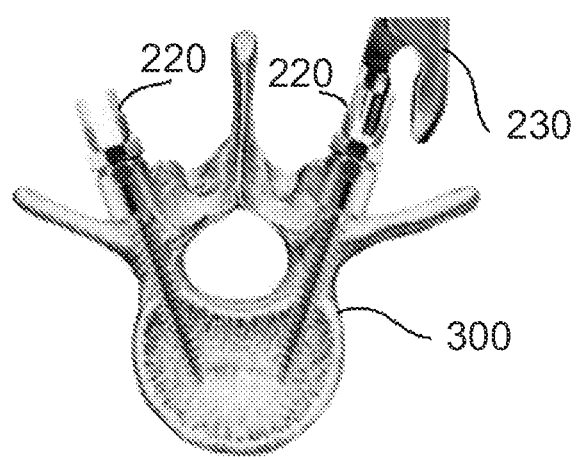
FIG. 4 shows pedicle screws inserted into a vertebra.

FIG. 4 shows two pedicle screws 220 placed in a vertebra 300 together with a tool 230 for screwing in the screws 220 into the bone. A screw insertion placement software and screw placement may show the vertebrae and a planned insertion line. Additionally and/or alternatively, the screw insertion placement may be shown guided by the cameras. The planned trajectory may be shown too and the position of the screw may be shown based on the navigation system. It is noted that an inside of a body may be shown based on an earlier taken image of the interior of the body, wherein the actual position of the vertebra may be different due to displacement of interior structures of the body compared to outer surface of the body.

Figure 5:
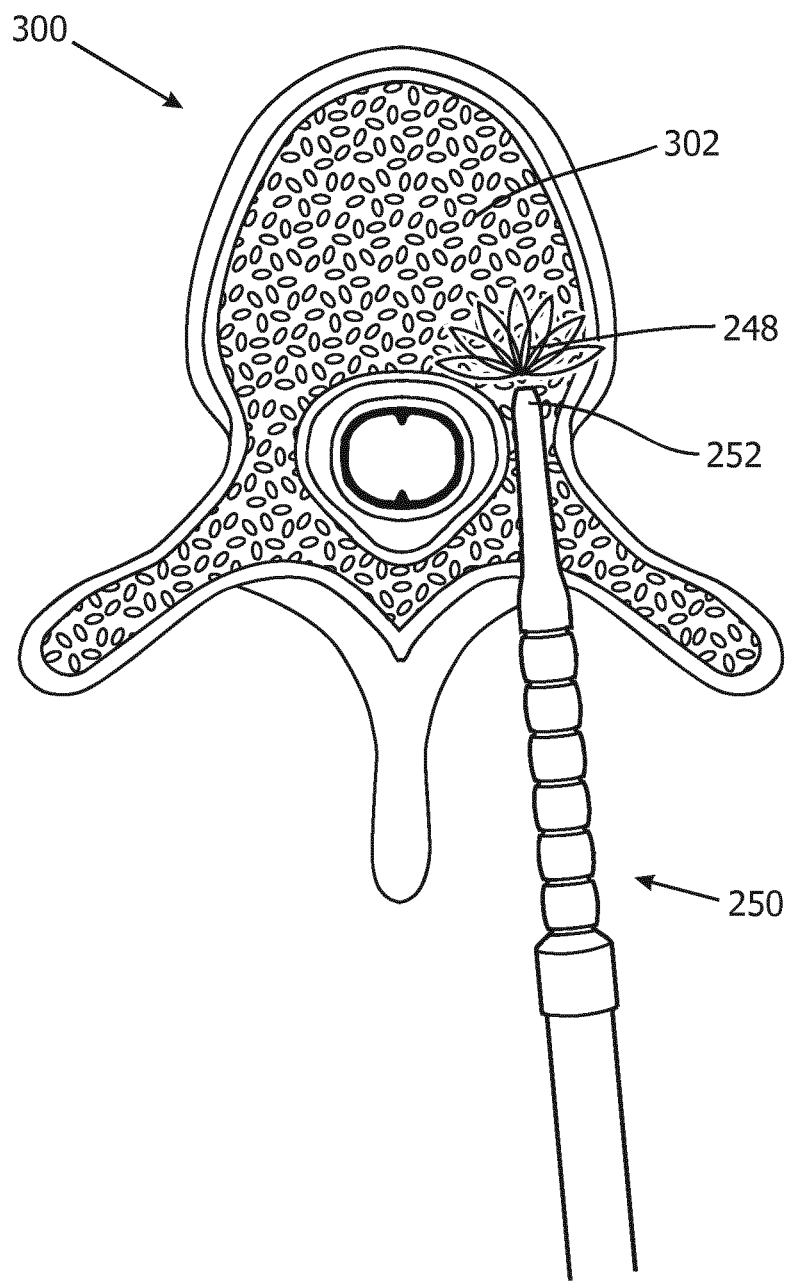
FIG. 5 is a view onto a vertebra with a device according to an embodiment.

In FIG. 5 an example of a model is illustrated, the model showing tissue structures that can be encountered during an insertion of a device. The device 250 should be in the vertebra 300 with the tip 252 in the cancellous bone 302. This cancellous bone has a higher fat content. Therefore for instance building a look up table based on the fat content of tissue can be used to guide the device placement. The fat content is a parameter that can be determined real-time with spectral tissue sensing 248. From the predicted fat content based on the device placement planning software and comparing this to the actual fat content based on the real-time determined fat content based on spectral tissue sensing is a way to determine the difference.

Figure 6:
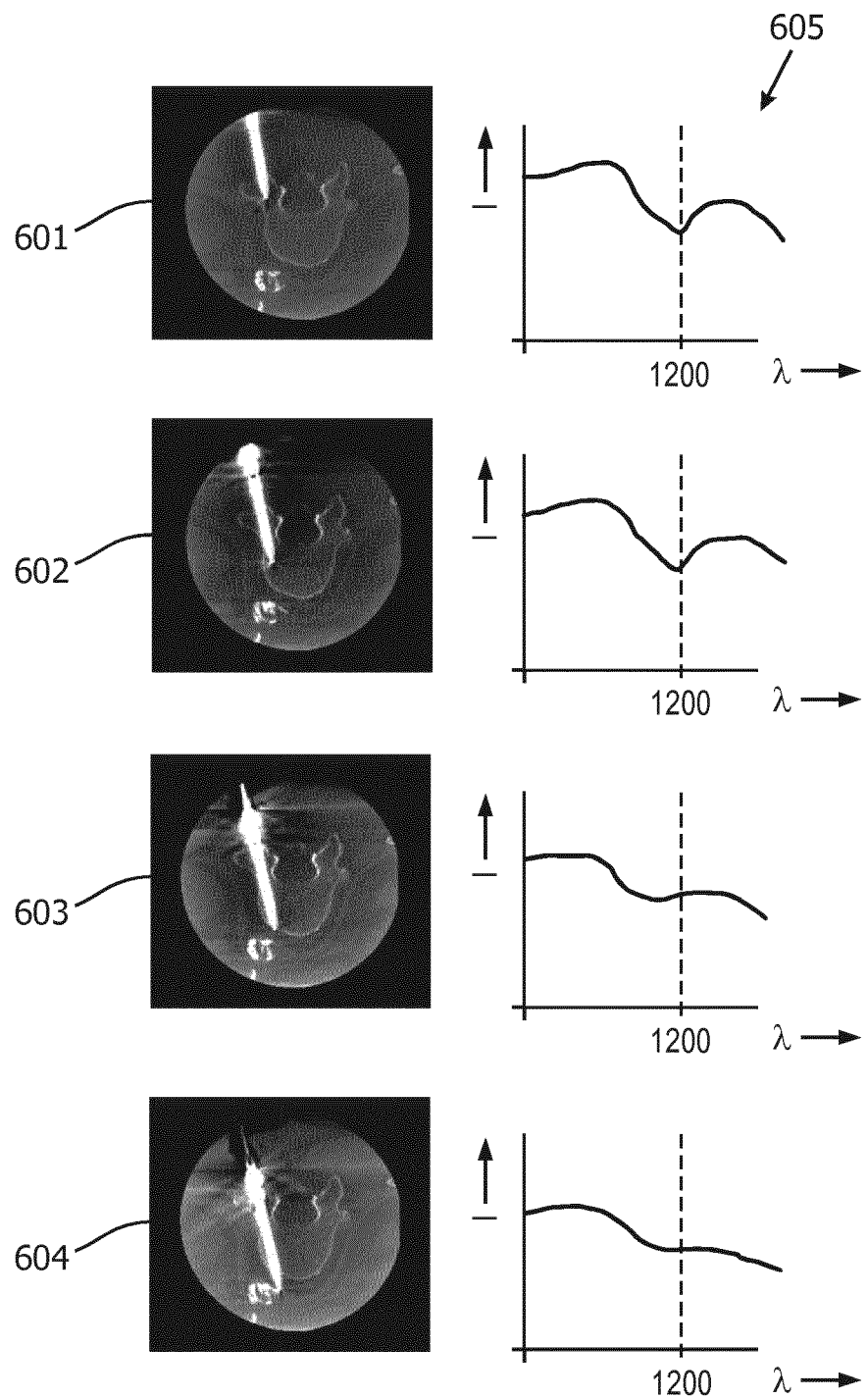
FIG. 6 shows a sequence of images and graphs illustrating different instances of an insertion of a pedicle screw into a vertebra of a spine.

FIG. 6 depicts four images 601, 602, 603, 604 from a sequence acquired during a screw insertion along with an example of acquired tissue measurements. In images 601, 602, the screw tip can be observed to be positioned in cancellous bone have a higher fat content while in images 603, 604, the screw tip is positioned in cortial bone where the fat content is lower.

When according to the position determined by the imaging/navigation system the screw tip should be in cortical bone while the spectral tissue analysis carried out by the sensing system does not confirm this the screw is regarded as being off track and a corresponding signal may be generated. Apart from fat content of the tissue, other parameters can be used as well for this. For instance, scattering may also reveal also a clear transition from cancellous to cortical bone that can be used as well.

As an example, parts of the spectrum of received light reflected by tissue surrounding the screw tip are represented in the graphs 605 at the right-hand side of the images 601, 602, 603, 604. In these graphs, on the horizontal axis, a wavelength (lambda) is represented in nanometer (nm), and on the vertical axis, an intensity (I) is represented in arbitrary units. For images 601 and 602, the relatively high fat content of the cancellous bone tissue in the vertebral body translates to a relatively pronounced minimum in the spectrum of the reflect light around a wavelength of 1200 nm.

The processing unit 126, to which a data storage may be connected, may transform the spectra measured by the light detector into physiological parameters that are indicative of the tissue state for the source-detector fiber combination. To determine whether a certain tissue is in front of the probe (or implantable device), the signal for the source-detector pair can be compared with a look-up-table. Another way is to translate the measured parameters into physiological parameters and define ranges for these parameters for each tissue type. Incorporating referral is made to Duck, F. A., "Physical properties of tissue: A 30 comprehensive reference book" (1990, Academic Press, Harcourt Brace Jovanovich, Publishers), where methods based on classification and regression tree (CART) analyses are described for classifying tissue based on these physiological parameters.

In general, spectra from a given tissue type tend to look similar. The respective tissue "fingerprint" (characteristic spectrum) may be used to discriminate between tissue types. Typically, the fingerprint (for example by fitting the concentration of characteristic chromophores or by calculating principal components) is firstly extracted/enhanced and then these derived features are used to discriminate tissues based on typical machine learning methods such as SVM, CART, cut-off values, or k-nearest-neighbors. For example, it is clear that fat spectra have a different characteristic shape (or fingerprint) than the muscle or bone tissue. For example, a dip in the reflected light intensity near a wavelength of 1200 nm is nearly always more pronounced for tissue with a relatively high fat content than for muscle or cortial bone tissue (cf. right column graphs 605 in FIG. 6).

An algorithm may be utilized to produce a table of tissue properties that may be encountered during the planned screw insertion. To determine the tissue properties, two approaches can be used: First, the vertebra of the spine may be segmented using a segmentation algorithm. An anatomical model (for example a model as shown in FIG. 5) may be applied to the segmented spine and may be used to calculate the expected spectral tissue measurements. Second, an imaging technique may be used that can measure fat content or other tissue properties that can be detected with spectral tissue sensing. The imaging technique may be acquired before the procedure such as a pre-operative MRI which is consequently registered to the navigation system. Subsequently, one or more image series may be used as input for an algorithm that calculates the expected spectral tissue measurements. These image series can be multiple contrasts from MRI of the same anatomy or the combination of multiple imaging modalities. Also MR spectrographic imaging can be used as input. It will be understood that the two approaches could be combined.

Figure 7:
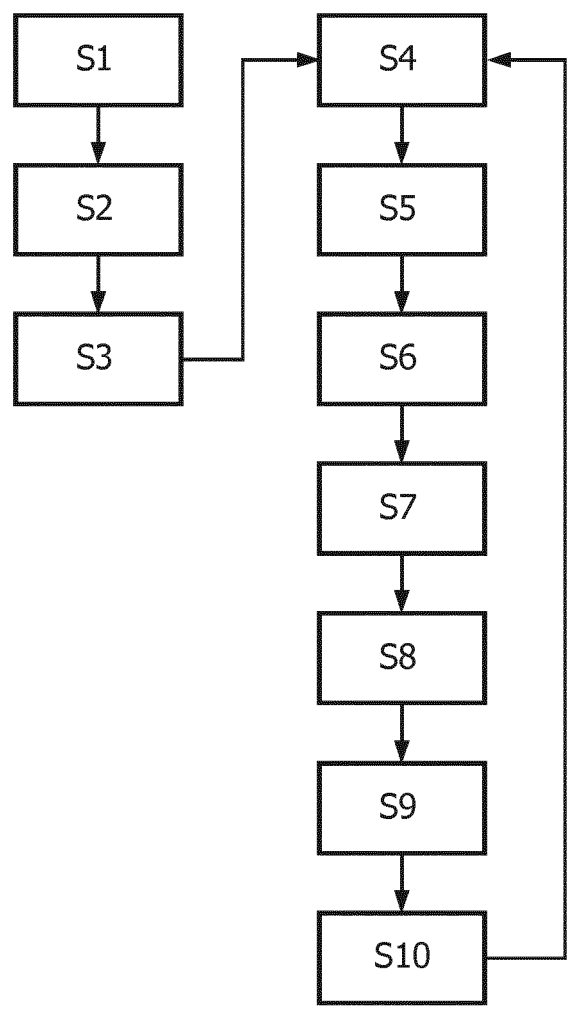
FIG. 7 is a flow chart illustrating steps of a method executable based on a computer program.

With reference to FIG. 7, a method, i.e. a software solution is described. The flowchart in FIG. 7 illustrates the principles of position determination in accordance with an embodiment. It will be understood that the steps described with respect to the computer based method are major steps, wherein these major steps might be differentiated or divided into several sub steps. Furthermore, there might be also sub steps between these major steps. A sub step is only mentioned if that step is important for the understanding of the principles of the method according to the invention.

In step S1, information of a region of interest including different tissue types are received by the processing unit. Such information may be received from a data base storing previously generated images and/or from an imaging device generating the information/data immediately before the receiving.

In step S2, an input is received identifying a path through the region of interest. Such an input may be done by a user by means of a touch screen, a computer mouse or a keyboard, by an indication directly in an image and/or by defining coordinates. Additionally and/or alternatively, the input may be generated automatically by the processing unit based on comparable procedures, i.e. the processing unit may suggest a path through the tissue. The user may then just individually adjust the path as needed.

In step S3, a sequence of tissue types along the path is determined. The sequence of steps S1 to S3 may be considered as a planning method.

In step S4, optical information are received from the optical sensing means at the tip of the device, during an insertion of the device along the determined path into the region of interest. This step may comprise the sub-steps of emitting light, receiving light and determining a light spectrum. In step S5, a tissue type at that distal end of the optical guide is determined based on the received optical information.

In step S6, the tissue type as determined in step S5 is compared with the pre-determined tissue types on the path (as determined in step S3).

Additionally, the distal end of the optical guide may be traced by means of a tracking device in step S7. In fact, a spatial position and orientation of a proximal, i.e. trailling end of the optical guide may be traced, for example by a camera imaging a tracer plate. The known geometry of the optical guide together with the determined proximal position and orientation allows for a determination of the distal end, even if that end is currently not visible.

In step S8, possible positions of the distal end of the optical guide on its path through the tissues are determined based on a comparison of tissue types and/or on the tracked position. Based on that determination, a signal can be generated indicative for the possible positions in step S9.

Optionally, a visualization of the region of interest together with a virtual representation of an element to be inserted in the region of interest may be generated in step S10, wherein the distal end of the virtual representation of the element is shown at the most probable position on the path in an image which may be generated previously, i.e. during a planning phase of the procedure.

It will be understood that steps S4 to S10 may be repeated, if necessary, for controlling an insertion of a device into a region of interest. It is noted that the advantage achieved by such a method can also be seen in a reduction of an X-ray exposure for a patient, as the controlling of the position of the inserted device is not primarily based on X-ray information.

Finally, it is noted that tissue sensing is not only relevant for screw insertions, but for many other clinical procedures as well. For instance, biopsies, deep brain stimulation placement, tumor ablation etc. Tissue sensing hardware can be envisaged for typical devices used in these procedures. By using advanced imaging and/or anatomical modelling it is possible to calculate expected spectral tissue measurements for most anatomical regions. By way of example, the following clinical applications will benefit from this invention: (i) pedicle screw insertions in the cervical, thoracic and lumbar spine, (ii) fracture fixations in various bone traumas, and (iii) plate positioning in hip and knee arthroplasties.

While the invention has been illustrated and described in detail in the drawings and foregoing description, such illustration and description are to be considered illustrative or exemplary and not restrictive; the invention is not limited to the disclosed embodiments. Other variations to the disclosed embodiments may be understood and effected by those skilled in the art in practicing the claimed invention, from a study of the drawings, the disclosure, and the appended claims.

In the claims, the word "comprising" does not exclude other elements and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

LIST OF REFERENCE SIGNS 102 system
104 X-ray device or system
106 base frame
108 wheels
110 C-arm
112 table
114 patient
116 first axis
118 second axis
120 X-ray source
122 X-ray detector
124 camera
126 processing unit
128 monitor
130 further camera
202 K-wire
204 leading end portion
206 trailling end portion
208 instrument
210 grip portion
212 handle
220 screw
222 body
224 neck
226 head
230 tool
240 optical sensing device
242 probe or stylet
244 optical guide or fiber
246 optical console
248 tissue sensing
250 device
252 tip of device
300 vertebra
302 cancellous bone

The invention claimed is:

1. A system for determining a position of an insertable medical device that is configured to be inserted into tissue of a patient during a medical procedure, comprising:
a positioning device configured to be inserted through a path of the region of interest of tissue of a patient to position the insertable medical device, the positioning device including:

an optical guide with a distal end, the optical guide being configured within the positioning device to emit light to a tissue segment at the distal end of the optical guide;

a light detector configured to be coupled to the optical guide and to detect light reflected by the tissue segment at the distal end of the optical guide as the positioning device is inserted through the path; and a processor operatively coupled to the positioning device and configured to:
  (i) receive tissue type information of the region of interest, including different tissue types of the region of interest,
  (ii) receive an input identifying the path to insert the positioning device through the region of interest,
  (iii) determine a sequence of tissue types along the identified path based on the received tissue type information of the region of interest,
  (iv) receive, from the light detector, the detected light of the tissue segment at the distal end of the optical guide as the positioning device is inserted into the region of interest,
  (v) determine a tissue type of the tissue segment at the distal end of the optical guide based on the detected light,
  (vi) determine possible positions of the positioning device along the path by comparing the determined tissue type of the tissue segment with the sequence of tissue types along the path, and generate a signal indicating the determined possible positions, and
  (vii) detect a mismatch between the determined tissue type of the tissue segment and predicted tissue types for the determined possible positions, and generate a signal indicating the mismatch for prompting a user to adapt the placement of the insertable medical device.

2. The system of claim 1, further comprising a tracking device for tracking a position of the distal end of the optical guide relative to the region of interest, wherein determination of the possible positions is further based on the tracked position.

3. The system of claim 2, wherein the tracking device comprises elements for electromagnetic tracking, optical tracking and/or shape sensing.

4. The system of claim 1, wherein the processor is further configured to generate a visualization of the region of interest together with a virtual representation of the insertable medical device, in the region of interest, wherein a distal end of the virtual representation of the device is shown at a most probable position on the path.

5. The system of claim 4, further comprising an instrument for inserting the device into the tissue, wherein a position and orientation of the instrument is traceable by the tracking device, and wherein the generated visualization includes an indication of a relation of the instrument to the region of interest.

6. The system of claim 1, further comprising a video camera for imaging an operation field including the region of interest, wherein the processor is further configured to generate a combined visualization of the operation field and of inner structures of the region of interest.

7. The system of claim 1, further comprising an imaging system for generating information of a region of interest including different tissue types, wherein the imaging system is a medical imaging system out of the group consisting of an X-ray imaging system, a magnetic resonance imaging system, a computed tomography imaging system, and an ultrasound imaging system.

8. The system of claim 1, wherein the insertable medical device is a device out of the group consisting of a screw, a K-wire, an awl, and a tap.

9. A method of determining a position, utilizing a positioning device, of an insertable medical device insertable that is configured to be inserted into tissue of a patient during a medical procedure, the method comprising:
  receiving tissue type information of a region of interest of tissue of a patient, including different tissue types and an input identifying a path to insert the insertable medical device through the region of interest,
  determining a sequence of tissue types along the identified path based on the received tissue type information of the region of interest,
  receiving, from a light detector coupled to the positioning device, detected light reflected from a tissue segment at a distal end of an optical guide of the positioning device, as the positioning device is inserted into the region of interest,
  determining a tissue type of the tissue segment at the distal end of the optical guide based on the detected light,
  determining possible positions of the positioning device along the path by comparing the determined tissue type of the tissue segment with the sequence of tissue types along the path, and generating a signal indicating the determined possible positions;
  detecting a mismatch between the determined tissue type at the distal end and predicted tissue types for the determined possible positions; and
  prompting a user to adapt the placement of the insertable medical device based on the detected mismatch.

10. The method of claim 9, further comprising the step of generating a visualization of the region of interest together with a virtual representation of the insertable medical device, in the region of interest, wherein a distal end of the virtual representation of the insertable medical device is shown at a most probable position on the path.

11. A computer program product comprising sets of instruction which, when executed on a processor of a system for determining a position of a device insertable into tissue according to claim 1, cause the processor to:
  (i) receive tissue type information of a region of interest of tissue of a patient, including different tissue types of the region of interest,
  (ii) receive an input identifying a path to insert the device through the region of interest,
  (iii) determine a sequence of tissue types along the identified path based on the received tissue type information of the region of interest,
  (iv) receive, from a light detector coupled to the device, detected light reflected from a tissue segment at a distal end of an optical guide of the positioning device, as the positioning device is inserted into the region of interest,
  (v) determine a tissue type of the tissue segment at the distal end of the optical guide based on the detected light,
  (vi) determine possible positions of the positioning device along the path by comparing the determined tissue type of the tissue segment with the sequence of tissue types along the path, and generate a signal indicating the determined possible positions, and
  (vii) detect a mismatch between the determined tissue type of the tissue segment and predicted tissue types for the determined possible positions, and generate a signal indicating the mismatch for prompting a user to adapt the placement of the insertable medical device.

\* \* \* \* \*